(12) United States Patent
Pittinger et al.

(10) Patent No.: US 8,523,750 B2
(45) Date of Patent: Sep. 3, 2013

(54) METHOD AND APPARATUS FOR EXTRACTING PLATELETS WITH REDUCED PLASMA CARRYOVER

(75) Inventors: John Pittinger, Evergreen, CO (US); Logan Fender, Lakewood, CO (US)

(73) Assignee: Terumo BCT, Inc., Lakewood, CO (US)

( * ) Notice: Subject to any disclaimer, the term of this patent is extended or adjusted under 35 U.S.C. 154(b) by 368 days.

(21) Appl. No.: 12/964,787

(22) Filed: Dec. 10, 2010

(65) Prior Publication Data
US 2011/0152055 A1 Jun. 23, 2011

Related U.S. Application Data

(60) Provisional application No. 61/288,744, filed on Dec. 21, 2009.

(51) Int. Cl.
*B04B 7/04* (2006.01)

(52) U.S. Cl.
USPC .................................. 494/45; 494/27; 494/30

(58) Field of Classification Search
USPC .................. 494/27, 30, 37, 42, 45; 210/782, 210/787; 604/5.01, 6.01, 4.01–6.16
See application file for complete search history.

(56) References Cited

U.S. PATENT DOCUMENTS

| | | | |
|---|---|---|---|
| 4,637,813 A | 1/1987 | Devries | |
| 5,653,887 A | 8/1997 | Wahl et al. | |
| 5,676,644 A | 10/1997 | Toavs et al. | |
| 5,702,357 A | 12/1997 | Bainbridge et al. | |
| 5,720,716 A | 2/1998 | Blakeslee et al. | |
| 5,722,946 A | 3/1998 | Mudloff et al. | |
| 5,738,644 A | 4/1998 | Holmes et al. | |
| 5,750,025 A | 5/1998 | Holmes et al. | |
| 5,795,317 A | 8/1998 | Brierton et al. | |
| 5,837,150 A | 11/1998 | Langley et al. | |
| 5,919,154 A | 7/1999 | Toavs et al. | |
| 5,921,950 A | 7/1999 | Toavs et al. | |
| 5,941,842 A | 8/1999 | Steele et al. | |
| 6,022,306 A | 2/2000 | Dumont et al. | |
| 6,129,656 A | 10/2000 | Blakeslee et al. | |
| 6,354,986 B1 * | 3/2002 | Hlavinka et al. | 494/45 |

(Continued)

FOREIGN PATENT DOCUMENTS
WO WO99/11305 3/1999

OTHER PUBLICATIONS

Salgaller, Michael L., "A Manifesto on the Current State of Dendric Cells in Adoptive Immunotherapy", *Transfusion*, 2003, 43(4):422-424.

(Continued)

*Primary Examiner* — Walter D Griffin
*Assistant Examiner* — Timothy Cleveland
(74) *Attorney, Agent, or Firm* — John R. Merkling

(57) ABSTRACT

A centrifugal blood processing apparatus comprising a centrifuge rotor, a separation chamber, a tubing set for conducting blood components and fluids and a method for controlling the blood processing apparatus comprising separating a blood component in a separation chamber; flowing the blood component out of the separation chamber and into a concentration chamber; concentrating the blood component in the concentration chamber; and flushing the blood component out of the concentration chamber. The method further comprising simultaneously flowing a solution, such as a wash solution or PAS, into the concentration chamber between the separation chamber and the concentration chamber.

6 Claims, 7 Drawing Sheets

(56) References Cited

U.S. PATENT DOCUMENTS

| | | |
|---|---|---|
| 7,052,606 B2 | 5/2006 | Gibbs et al. |
| 7,686,779 B1 | 3/2010 | Gibbs |
| 2009/0166298 A1 | 7/2009 | Fender |
| 2009/0259162 A1 | 10/2009 | Ohashi et al. |

OTHER PUBLICATIONS

PCT/US2010/059787, "International Search Report", mailed Jan. 6, 2012.

PCT/US2010/059787, "Written Opinion", mailed Jan. 6, 2012.

\* cited by examiner

METHOD AND APPARATUS FOR EXTRACTING PLATELETS WITH REDUCED PLASMA CARRYOVER

RELATED APPLICATIONS

This application claims the benefit of U.S. Provisional Application No. 61/288,744 filed Dec. 21, 2009.

FIELD OF INVENTION

The present invention relates generally to the field of extracorporeal blood processing methods and apparatus which are particularly useful in blood component collection, and more particularly, the present invention relates to methods and apparatus for centrifugally extracting platelets from other blood components with reduced plasma content, preferably with the addition of a Platelet Additive Solution (PAS).

BACKGROUND OF THE INVENTION

One well-known type of extracorporeal blood processing involves an aphaeresis system and procedure in which blood is removed from a donor or a patient (hereafter cumulatively referred to as a donor), directed to a blood component separation device (e.g., centrifuge), and separated into various blood component types (e.g., red blood cells, white blood cells, platelets, plasma) for collection or therapeutic purposes. One or more or all of these blood component types may either be collected and treated for therapeutic purposes before storage or returned to a patient, while the remainder may simply be returned to the donor or patient.

A number of factors may affect the commercial viability of an aphaeresis system. One factor relates to the time and expertise required of an individual to prepare and operate the aphaeresis system. For instance, reducing the time required by the operator to complete an entire collection procedure, as well as reducing the complexity of these actions, can increase productivity or lower the potential for operator error. Moreover, reducing the dependency of the system on the operator may further lead to reductions in the credentials desired/required for the operators of these systems.

Performance-related factors also affect the commercial viability of an aphaeresis system. Performance may be judged in terms of the collection efficiency of the aphaeresis system, which may impact or improve product quality and/or may in turn reduce the amount of processing time and thus decrease operator burden and increase donor convenience. The collection efficiency of a system may of course be gauged in a variety of ways, such as by the amount of a particular blood component type which is collected in relation to the quantity of this blood component type which passes through the aphaeresis system. Performance may also be evaluated based upon the effect which the aphaeresis procedure has on the various blood component types. For instance, it is desirable to minimize the adverse effects on the blood component types as a result of the aphaeresis procedure.

In particular, concerns have arisen regarding plasma-induced transfusion reactions in certain patients. Efforts have been made to produce platelet components (or "products") with lower plasma concentration and with PAS used as a storage solution. Such platelet products may have high platelet concentrations, for example between 3000 and 5000 platelets per milliliter. There remains a need, however, to produce a platelet product with as little residual plasma as possible, thereby reducing or eliminating plasma-induced transfusion reactions.

An apparatus and method for red blood cell filtration in conjunction with aphaeresis separation is also disclosed in the commonly-owned U.S. patent application Ser. No. 09/672,519, filed Sep. 27, 2000, herein incorporated by reference. Further background on aphaeresis red blood cell separation and collection can be found in the PCT publication WO99/11305, which is also incorporated herein by this reference. Commonly-owned U.S. Pat. No. 7,052,606 is directed to red blood cell filtration, but also discusses the need to add storage solution to a collected blood component and certain means whereby storage solution may be added to the collected component. Commonly-owned U.S. patent application Ser. No. 12/234,960 (Publication US2009/0166298) describes the controlled addition of PAS to a blood component.

SUMMARY OF THE INVENTION

The present invention generally relates to extracorporeal blood processing and particularly to an apparatus for producing a concentrated platelet product having a reduce plasma content. Multiple chambers are mounted on a centrifuge rotor, comprising a separator or LRS chamber and a concentrator or concentration chamber. The chambers are connected such that blood components may be selectively processed through only one chamber or through both chambers. Since each of the various aspects of the present invention may preferably be incorporated into an aphaeresis system (e.g., whether for blood component collection in which "healthy" cells or other blood components are removed from the donor blood for later transfusion, or for therapeutic "unhealthy" blood component removal), the present invention will be described in relation to such aphaeresis systems. Aphaeresis may often imply the return of certain blood components back to the donor. However, certain aspects of the present invention may be suited for extracorporeal blood processing applications in which all donated blood components are retained and such are also intended within the scope of the present invention.

An apheresis system which may be used with one or more aspects of the present invention generally includes at least a blood component separation device (a membrane-based separation device, and/or a rotatable centrifuge element, such as a rotor and channel combination), which provides the mechanism and/or the forces required to separate blood into various blood component types, such as red blood cells, white blood cells, platelets, or plasma. In one preferred embodiment, the separation device includes a centrifuge channel which receives a disposable blood processing vessel. Typically, a donor is fluidly interconnected with the blood processing vessel by an extracorporeal tubing circuit, and preferably the blood processing vessel and extracorporeal tubing circuit collectively define a closed, sterile system. When the fluid interconnection is established, blood may be extracted from the donor and directed to the blood component separation device such that at least one type of blood component may be separated and removed from the blood, either for collection or for therapy. An additive or storage solution is added to the red blood cells or platelets. A blood return reservoir has heretofore been used to receive selected blood components before returning those components to the donor. Controls may be provided to prime parts of a blood processing tubing and collection assembly with storage solution after the collection of selected blood components. Certain connections in the blood processing tubing and collection assembly allow storage solution to be flushed past peristaltic pumps into the return reservoir. Sensors in the return reservoir are used to confirm the presence of storage solution and to calibrate the solution within the tubing and collection assembly. A controlled volume of the additive or storage solution can then be pumped into a storage bag containing red blood cells or platelets. The volume is controlled or metered by the action of peristaltic pumps, which move a known quantity of fluid per pump revolution. The apparatus confirms the presence of storage solution in the system before pumping the storage solution into bags containing collected blood components. Alternatively, storage solution may be added during collection of components. Self-priming with storage solution and metered delivery of solution reduces the requirements for operator intervention and possible error and improves the accuracy of blood component mixing with storage solution.

It is a feature of the invention to provide a blood processing apparatus comprising a centrifuge rotor; and a disposable set having a separation chamber mounted on said centrifuge and having an outlet line at least part of the outlet line extending off of said centrifuge rotor; a solution line in fluid communication with said at least one outlet line, and a collection chamber, the collection chamber having an inlet and an outlet, the outlet of said separation chamber being in fluid communication with the inlet of said collection chamber.

It is another aspect of the invention to provide a solution line connected between the outlet of the separation chamber and the inlet of the collection chamber.

Yet another aspect of the invention is to provide at least one blood component collection bag in fluid communication with the outlet of the collection chamber.

Another element of the invention may be means for flushing blood components out of the collection chamber into the collection bag and for simultaneously restraining fluid from flowing out of the separation chamber.

In another aspect, a blood processing vessel may be provided for receiving whole blood, said blood processing vessal having an outlet, wherein the blood processing vessel outlet is in fluid communication of the inlet of the separation chamber.

The invention may also included a method for controlling a blood processing apparatus comprising separating a blood component in a separation chamber; flowing the blood component out of the separation chamber and into a concentration chamber; concentrating the blood component in the concentration chamber; and flushing the blood component out of the concentration chamber.

The method may further comprise flowing a solution into the concentration chamber between the separation chamber and the concentration chamber.

The method may also include mounting both the separation chamber and the concentration chamber a centrifuge rotor and simultaneously adding wash or platelet additive solution to and removing the solution from the concentration chamber.

These and still further aspects of the present invention are more particularly described in the following description of the preferred embodiments presented in conjunction with the attached drawings which are described briefly below.

DETAILED DESCRIPTION

The present invention will be described in relation to the accompanying drawings. Generally, the primary aspects of the present invention relate to both procedural and structural improvements in or to a sub-assembly for use with a blood processing aphaeresis system. However, certain of these improvements may be applicable to other extracorporeal blood processing applications whether any blood components are returned directly to the donor or otherwise; and such are within the scope of the present invention as well.

Figure 1:
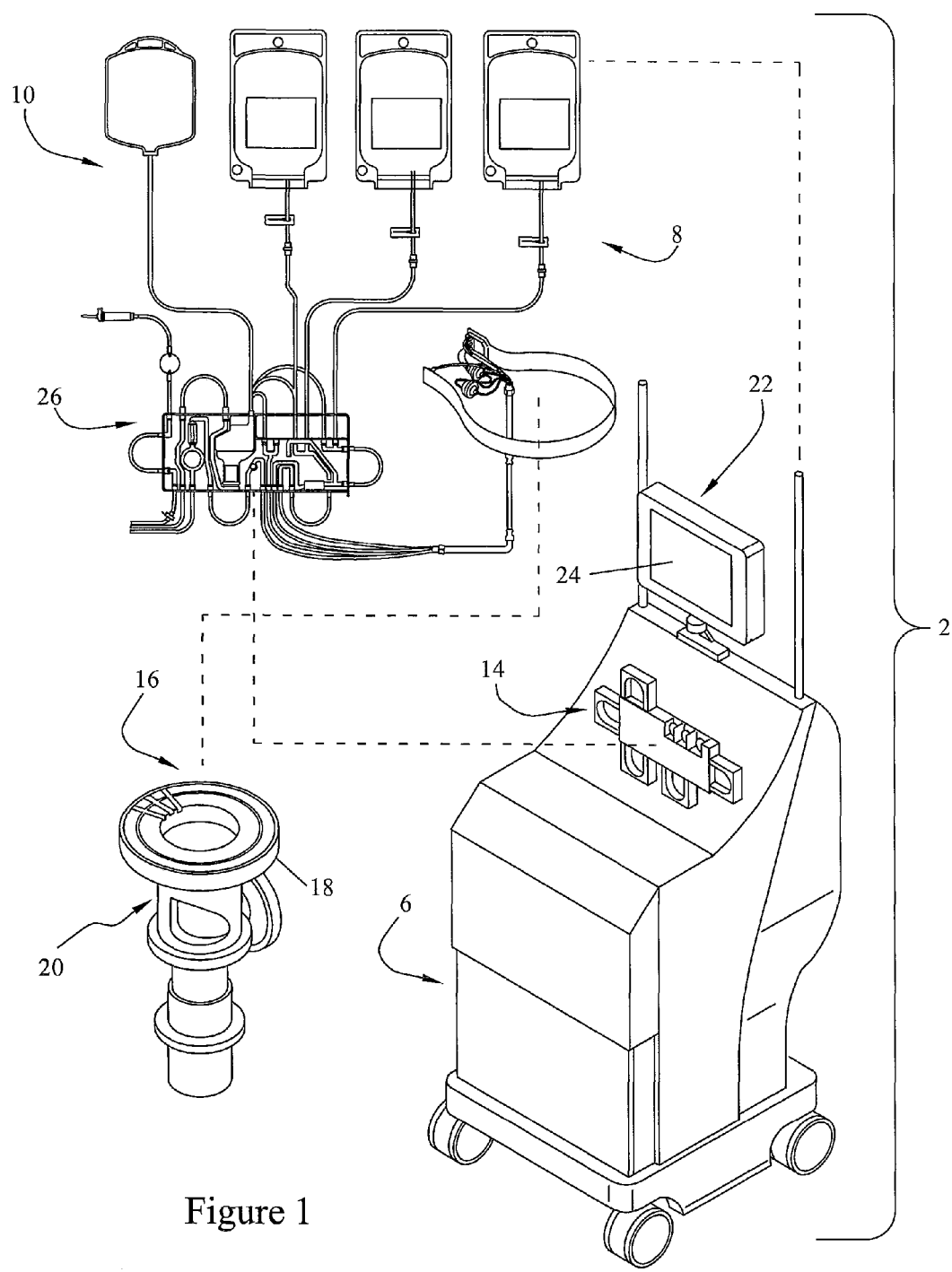
FIG. 1 is a schematic view of an aphaeresis system.

A preferred blood aphaeresis system 2 for use in and/or with the present invention is schematically illustrated in FIG. 1. System 2 preferably provides for a continuous blood component separation process. Generally, whole blood is withdrawn from a donor and is substantially continuously provided to a blood component separation device 6 where the blood is continuously separated into various component types and at least one of these blood component types is preferably continuously collected from the device 6. One or more of the separated blood components may then either be provided for collection and subsequent use by another through transfusion or may be uncollected and then returned to the donor. Therapeutic treatment and near immediate return of certain separated blood components is a viable, yet less common alternative use as well. It is also understood that for therapeutic treatment the blood may be separated into components with filtration using the principles of the instant invention and as described below at a patient's bedside for return to such patient.

In the blood aphaeresis system 2, blood is withdrawn from the donor and directed through a pre-connected bag and tubing set 8 which includes an extracorporeal tubing circuit 10 and, in one embodiment, a blood processing vessel 12 which together define a closed, sterile and disposable system. The set 8 is preferably disposable and is adapted to be mounted on and/or in the blood component separation device 6. The separation device 6 preferably includes a pump/valve/sensor assembly 14 for interfacing with the extracorporeal tubing circuit 10, and a channel assembly 16 for interfacing with the disposable blood processing vessel 12.

The channel assembly 16 may include a channel housing 18 that is rotatably interconnected with a rotatable centrifuge rotor assembly 20, which provides the centrifugal forces required to separate blood into its various blood component types by centrifugation. The blood processing vessel 12 may be fitted within the channel housing 18. When connected as described, blood can be flowed substantially continuously from the donor, through the extracorporeal tubing circuit 10, and into the rotating blood processing vessel 12. The blood within the blood processing vessel 12 may then be continuously separated into various blood component types and at least one of these blood component types (platelets, plasma, or red blood cells) is preferably continually removed from the blood processing vessel 12. Blood components which are not being retained for collection or for therapeutic treatment are preferably also removed from the blood processing vessel 12 and returned to the donor via the extracorporeal tubing circuit 10. Various alternative aphaeresis systems (not shown) may also make use of the present invention, including batch processing systems (non-continuous inflow of whole blood or non-continuous outflow of separated blood components) or smaller scale batch or continuous RBC/plasma separation systems, whether or even if no blood components may be returned to the donor.

Operation of the blood component separation device 6 is preferably controlled by one or more processors included therein, and may advantageously comprise a plurality of embedded computer processors to accommodate interface with ever-increasing PC user facilities (e.g., CD ROM, modem, audio, networking and other capabilities). In order to assist the operator of the aphaeresis system 2 with various aspects of its operation, the blood component separation device 6 preferably includes a graphical interface 22 with an interactive touch screen 24.

Further details concerning the operation of a preferred aphaeresis system, such as the Gambro Trima® System and the Trima® Accel™ System (available from the assignee of this application, Gambro BCT, Inc., Lakewood, Colo.) may be found in a plurality of publications, including, for example, WO99/11305 and U.S. Pat. Nos. 5,653,887; 5,676,644; 5,702,357; 5,720,716; 5,722,946; 5,738,644; 5,750,025; 5,795,317; 5,837,150; 5,919,154; 5,921,950; 5,941,842; and 6,129,656; among numerous others. The disclosures are incorporated herein. A plurality of other known aphaeresis systems may also be useful herewith, as for example, the Baxter CS3000®, Amicus®, Autopheresis-C®, and Alyx systems or the Haemonetics MCS® and MCS®+, or the Fresenius COM.TEC™ and AS-104™ or like systems.

Disposable Set: Extracorporeal Tubing Circuit

Figure 2:
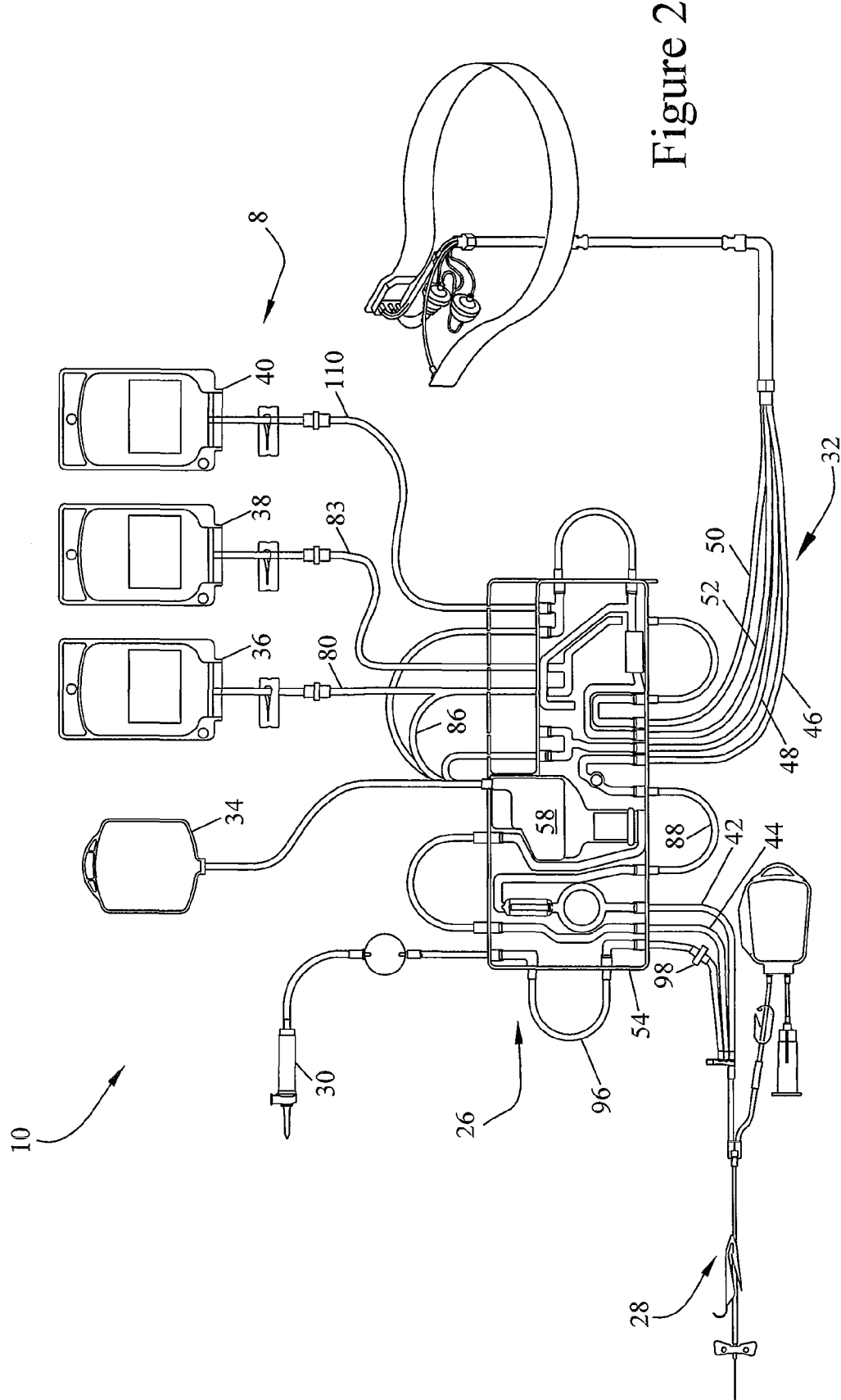
FIG. 2 illustrates a tubing and bag set including an extracorporeal tubing circuit, a cassette assembly, and collection bag assembly for use with the system of FIG. 1, pursuant to the present invention.
Figure 3:
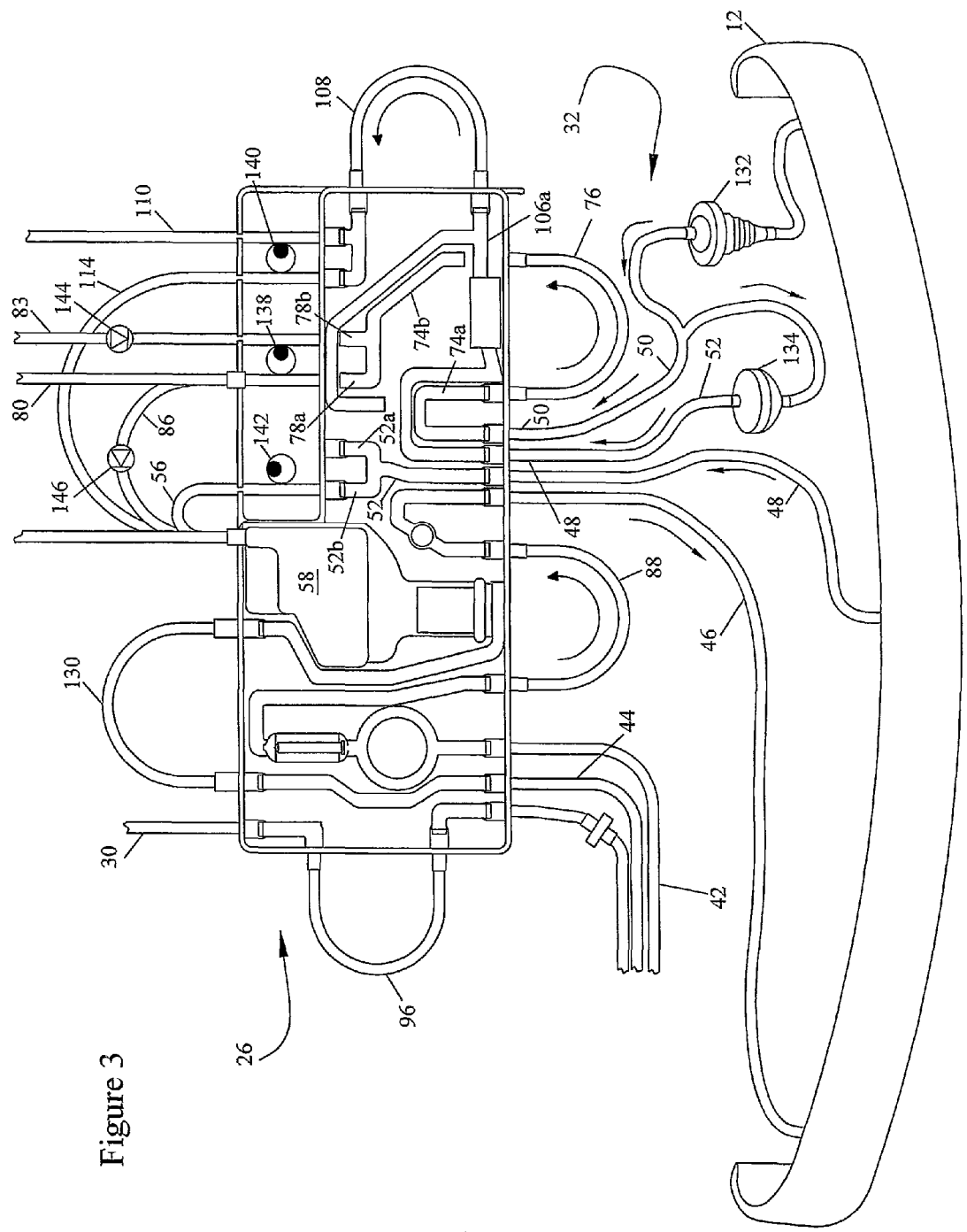
FIG. 3 illustrates a cassette assembly as shown in the set of FIG. 2, with fluid flow directions and valve status indicated.

As illustrated in FIGS. 2 and 3, the pre-connected extracorporeal tubing circuit 10 is shown which may include a cassette assembly 26 and a number of tubing/collection assemblies 28, 30, 32, 34, 36 and 40 interconnected therewith. Preferably, a blood removal/return tubing assembly 28 provides a single needle interface between a donor and the remainder of the tubing circuit 10 (although a two-needle set-up may also be used, not shown). At least two lines 42, 44 are provided in assembly 28 (see FIG. 3) for removal of blood from and return of components to the donor. This embodiment includes a cassette assembly 26, which is interconnected between the tubing assembly 28, which connects the donor thereto, and blood inlet/blood component outlet tubing line sub-assembly 32, which provides the interface between cassette assembly 26 and blood processing vessel 12. Four lines 46, 48, 50 and 52 are shown in FIGS. 2 and 3 for transport of blood and components to and from the processing vessel 12. An anticoagulant tubing assembly 30, a plasma collection tubing and bag assembly 36, a PAS solution bag 38, a vent bag tubing line sub-assembly 34, and a platelet assembly 40 are also interconnected with cassette assembly 26 in this embodiment. As will be appreciated, the extracorporeal tubing circuit 10 and blood processing vessel 12 are preferably pre-interconnected to yield a closed, pre-sterilized disposable assembly for a single use.

Emanating from vessel 12 is an RBC outlet tubing line 48 of the blood inlet/blood component tubing assembly 32 which is interconnected with integral RBC passageway 52 of cassette 54 of cassette assembly 26 (see FIGS. 2 and 3). The integral RBC passageway 52 includes first and second spurs 52a and 52b, respectively. The first spur 52a is interconnected with RBC return tubing loop 56 to return separated RBCs to a donor. For such purpose, the RBC return tubing loop 52 is preferably interconnected to the top of a blood return reservoir 58 of the cassette assembly 26. The second spur 52b may, as preferred herein, be closed.

In a portion of the cassette assembly 26, plasma tubing 50 of blood inlet/blood component tubing assembly 32 (see FIGS. 2 and 3) interconnects with a first integral plasma passageway 74a (see FIG. 3) of cassette assembly 26 (note, this is preferably a plasma collection sub-system; however, other components such as platelets could alternatively be collected here or with a similar arrangement). Cassette assembly 26 further includes a pump-engaging, plasma tubing loop 76 interconnecting the first integral plasma passageway 74a and a second integral plasma passageway 74b. The second integral plasma passageway 74b includes first and second spurs 78a and 78b. The first spur 78a is interconnected to the plasma collection tubing assembly 36 via tubing line 80. The plasma collection tubing assembly 36 may be employed to collect plasma during use and includes plasma collector tubing 80 and plasma collection bag 82. A slide clamp 84 (see FIG. 2) may be provided on plasma collector tubing 80. The second spur 78b of the second integral plasma passageway 74b is interconnected to a plasma return tubing loop 86 to return plasma to donor/patient. For such purpose, the plasma return tubing loop 86 is interconnected through loops 108 and 114 to the top of the blood return reservoir 58 of the cassette assembly 26. One or more types of uncollected blood components, e.g., plasma and/or platelets, collectively referred to as return blood components, will cyclically accumulate in and be removed from reservoir 58 during use. Here also, valve/clamp access is made through cassette assembly 26 to maintain the plasma collector tubing 80 and plasma return tubing loop 86 in a predetermined spaced relationship for flow control therethrough.

Most portions of the tubing assemblies 28, 30, 32, 36, 34, 38, and 40 and cassette assembly 26 are preferably made from plastic components including, for example, polyvinyl chloride (PVC) tubing lines, that may permit visual observation and monitoring of blood/blood components during use. It should be noted that thin-walled PVC tubing may be employed for approved, sterile docking (i.e., the direct connection of two pieces of tubing line) for the RBC collector tubing lines 60, inter alia. All tubing lines are pre-connected before sterilization of the total disposable assembly to assure that maximum sterility of the system is maintained. A highly desirable advantage of pre-connection of all of the elements of the tubing circuit including the collection bags involves the complete pre-assembly and then sterilization hereof after pre-assembly such that no sterile docking is later necessary (spike addition of storage solution excepted). Thus, the costs and risks of sterile docking are eliminated. Alternatively, thicker-walled PVC tubing may be employed for approved, sterile docking RBC collector tubing lines 60, inter alia.

As mentioned, a cassette assembly 26 in the embodiment of FIG. 3, may be mounted upon and operatively interface with the pump/valve/sensor assembly 14 of a blood component separation device 6 during use. Further details of an aphaeresis system set-up including the loading and interaction of a disposable assembly 8 with a blood component separation device 6, may be found in the above-listed patents, inter alia, and are not exhaustively repeated here.

Operation of Extracorporeal Tubing Circuit and Blood Component Separation Device Priming and various other operations of the aphaeresis process are preferably carried out as set forth in the above-listed patents. During a blood removal, whole blood will be passed from a donor into tubing line 44 of blood removal/return tubing assembly 28 and is then transferred to the blood component separation device 6. At device 6, the blood is flowed, preferably pumped via loop 88 (see FIG. 3), to the processing vessel 12 via the cassette assembly 26 and line 46 of the blood inlet/blood component tubing assembly 32 (FIGS. 2 and 3). Separation processing then occurs on a substantially continuous basis in vessel 12; i.e., blood flows therein, is separated and flows as separated components therefrom. After separation processing in vessel 12 (though separation is continuously occurring), uncollected blood components are transferred from the processing vessel 12 to and through cassette assembly 26, into and may then accumulate in reservoir 58 (FIGS. 2 and 3) of cassette 26 up to a predetermined level at which the blood component separation device 6, in a single needle operation, may (though in a continuous system, need not) pause the blood removal submode and initiate a blood return submode wherein these uncollected and/or treated components may be returned to the donor. As such, these accumulated components may be transferred into the blood return tubing line 44 of blood removal/return tubing assembly 28 and back into the donor. During the single needle blood return mode, when the accumulated return blood components in reservoir 58 are removed down to a predetermined level, blood component separation device 6 will then automatically end the blood return submode. This preferably will also automatically serve to reinitiate or continue the blood removal submode. The cycle between blood removal and blood return submodes will then continue until a predetermined amount of collected blood components have been harvested. In an alternative dual needle scheme, as is known in the art, blood may be continually removed from and blood components continually returned to a donor. The detailed mechanisms for such operations, including controlling the pumps, for example, are not shown or described in detail herein.

Also, certain components may be collected simultaneously or consecutively one after the other. In one example, platelets may be collected concurrently with plasma. In the primary example shown in the figures, two components are shown being collected, plasma in assembly 36 and platelets in the other collection assembly 40. When a sufficient quantity of one or the other is collected, further separated portions of such a component are returned to the donor with any other uncollected components, until a sufficient quantity of all components are collected. One or two selected components may be collected with all other components being returned to the donor.

With specific reference to FIGS. 2 and 3, in normal operation, whole blood will pass from the donor through the needle and blood removal tubing assembly 28, cassette assembly 26 and blood inlet tubing line 46 to processing vessel 12. The whole blood will then be separated in vessel 12. Also, a platelet stream or a plasma stream may be separated herein and be either collected in a collection assembly 40 or 36, or diverted to reservoir 58 for ultimate return to the donor. Separated plasma may be flowed through cassette 26 via loop 76 and line 80 for collection in the container 82 for plasma or diverted through loop 86 to reservoir 58. Separated platelets may be flowed through cassette 26 via loop 108 and line 110 for collection in the container 112 or diverted to reservoir 58 through loop 114. Further, red blood cells (including potentially some white blood cells) may be separated in and passed from vessel 12 through RBC outlet tubing line 48, through cassette assembly 26 and loop 56, and into reservoir 58.

Aphaeresis Protocol

One preferred protocol, which may be followed for performing an aphaeresis procedure relative to a donor utilizing the described system 2, will now be summarized. Initially, an operator loads the disposable plastic assembly 8 in and/or onto the blood component separation device 6. According hereto, the operator hangs the various bags on hooks on the blood component separation device 6. If one is used, the operator then also loads the cassette assembly 26 on the device 6 and/or the blood processing vessel 12 within the channel housing 18 as mounted on the centrifuge rotor assembly 20 in the machine 6.

With the extracorporeal tubing circuit 10 and the blood processing vessel 12 loaded in the described manner, the donor may then be fluidly interconnected with the extracorporeal tubing circuit 10 by inserting an access needle of the needle/tubing assembly 28 into the donor. In addition, the anticoagulant tubing assembly 30 (see FIG. 2) is primed and the blood removal/return tubing assembly 28 is primed preferably with blood from the donor. The blood processing vessel 12 is also primed for the aphaeresis procedure. In one embodiment, a blood prime may be used in that blood will be the first liquid introduced into the blood processing vessel 12. During the priming procedure, as well as throughout the remainder of the aphaeresis procedure, blood may be flowed into the vessel 12, blood components are separated from each other and one or more components is removed from the blood processing vessel 12.

The preferred blood aphaeresis system 2 provides for contemporaneous separation of a plurality of blood components during blood processing, including the separation of platelets and plasma, but optionally may provide for the separation and collection of platelets. In turn, such separated blood components may be selectively collected in corresponding storage reservoirs or immediately or after a minor delay returned to the donor during respective blood return submodes (or substantially constantly in a two-needle setup).

In a priming phase, illustrated in FIG. 3, the donor's blood may flow through line 42 and into the pump loop 88, where a peristaltic pump drives the whole blood through line 46 into the blood processing vessel 12. Alternatively, saline or another suitable solution may be used to prime the apparatus, rather than the donor's blood. As the vessel 12 fills with blood and separation begins under the influence of centrifugal force, red blood cells flow out line 48, through the passage 52 in the cassette and through the return loop 56 into the reservoir 58. From time to time, blood components will be pumped out of the reservoir 58 by a peristaltic pump acting on a return loop 130. Blood components are returned to the donor through line 44. Platelets and plasma leave the separation vessel 12 and enter a first stepped LRS or separation chamber 132 for initial separation. Under the influence of valves that engage tubes on the cassette 26, as will be explained hereafter, fluid leaving the separation chamber 132 fills both a second, or concentration chamber 134 and a return path comprising the tube 50, internal passage 74a, pump-engaging loop 76, internal passage 74b, and return loop 136, which is coupled to the reservoir 58. The concentration chamber does not need to have a stepped side wall. The PAS solution line 83 is closed to flow in an outward direction with a one-way valve 144 and the plasma line 86 is closed by a pivoting valve 138 on the pump/valve/sensor assembly 14. Fluid from the concentration chamber 134 flows through line 52 to an internal passage 106a on the cassette 26, through pump-engaging loop 108 and return loop 114 to the reservoir 58. Valve 140 temporarily closes the platelet line 110.

Figure 4:
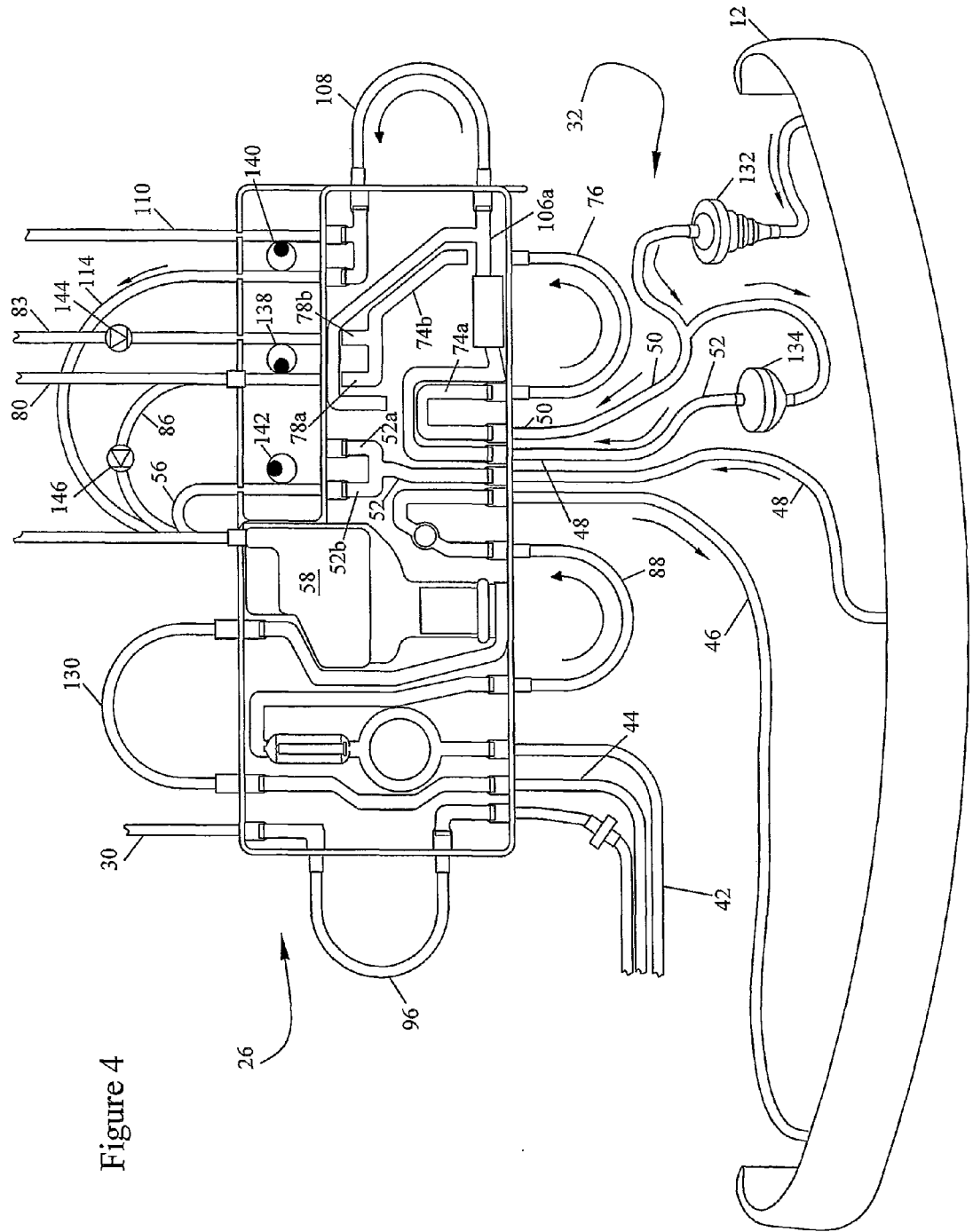
FIG. 4 shows the cassette assembly of FIG. 3 with a second state of fluid flow directions and valve status.

After priming, plasma can be collected while platelets are accumulating in the separation or LRS chamber 132. As shown in FIG. 4, whole blood is still driven through loop 88 into the blood processing vessel 12. Plasma is collected from the separation chamber 132 by action of the pump on loop 76. Valve 138 rotates to open tube 86 and close both tube 83 and return loop 136. In addition, some plasma may be drawn from the concentration chamber 134 for return to the donor through loop 114 and reservoir 58. The relative rates of withdrawal from the two chambers depend on the relative speed of peristaltic pumps acting on loop 76 and loop 108. While the plasma is collected, platelets accumulate in the separation chamber 132. Alternatively, plasma may be collected or returned to the donor from either the first or second chamber 132, 134.

Figure 5:
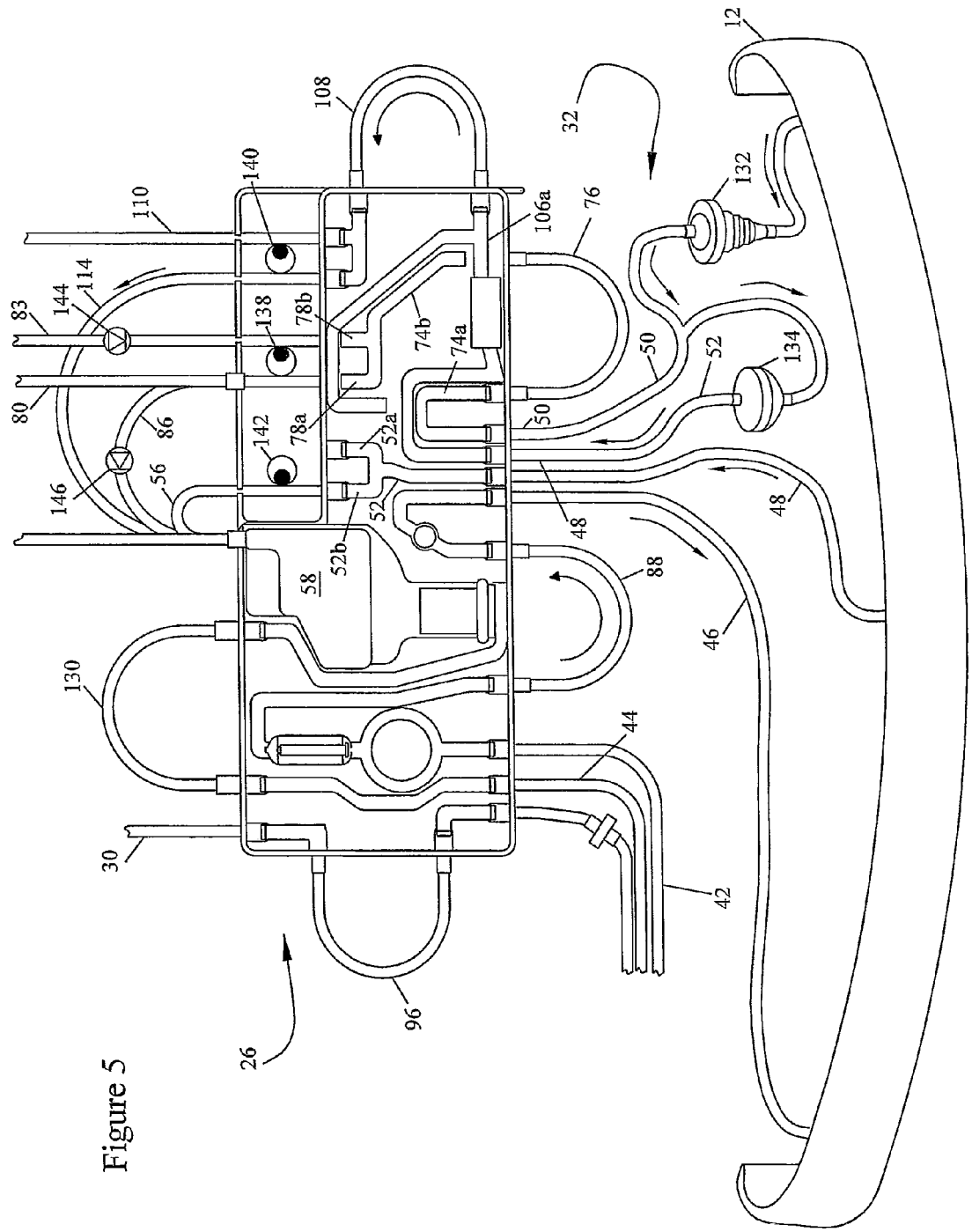
FIG. 5 shows the cassette assembly of FIG. 3 with a third state of fluid flow directions and valve status.

After the separation chamber 132 is filled or saturated with platelets, platelets begin to spill over out of the first chamber, as shown in FIG. 5. In this phase, the peristaltic pump driving loop 76 is stopped, blocking further collection of plasma. In addition, valve 138 is again rotated to open return loop 136 and close plasma collect tube 86. The PAS solution line 83 remains blocked by the one-way valve 144. Platelets flow into the concentration chamber 134 and begin to accumulate therein. Plasma is withdrawn from the concentration chamber 134 by pump action on the loop 108 and is returned to the donor through return loop 114 and reservoir 58.

Figure 6:
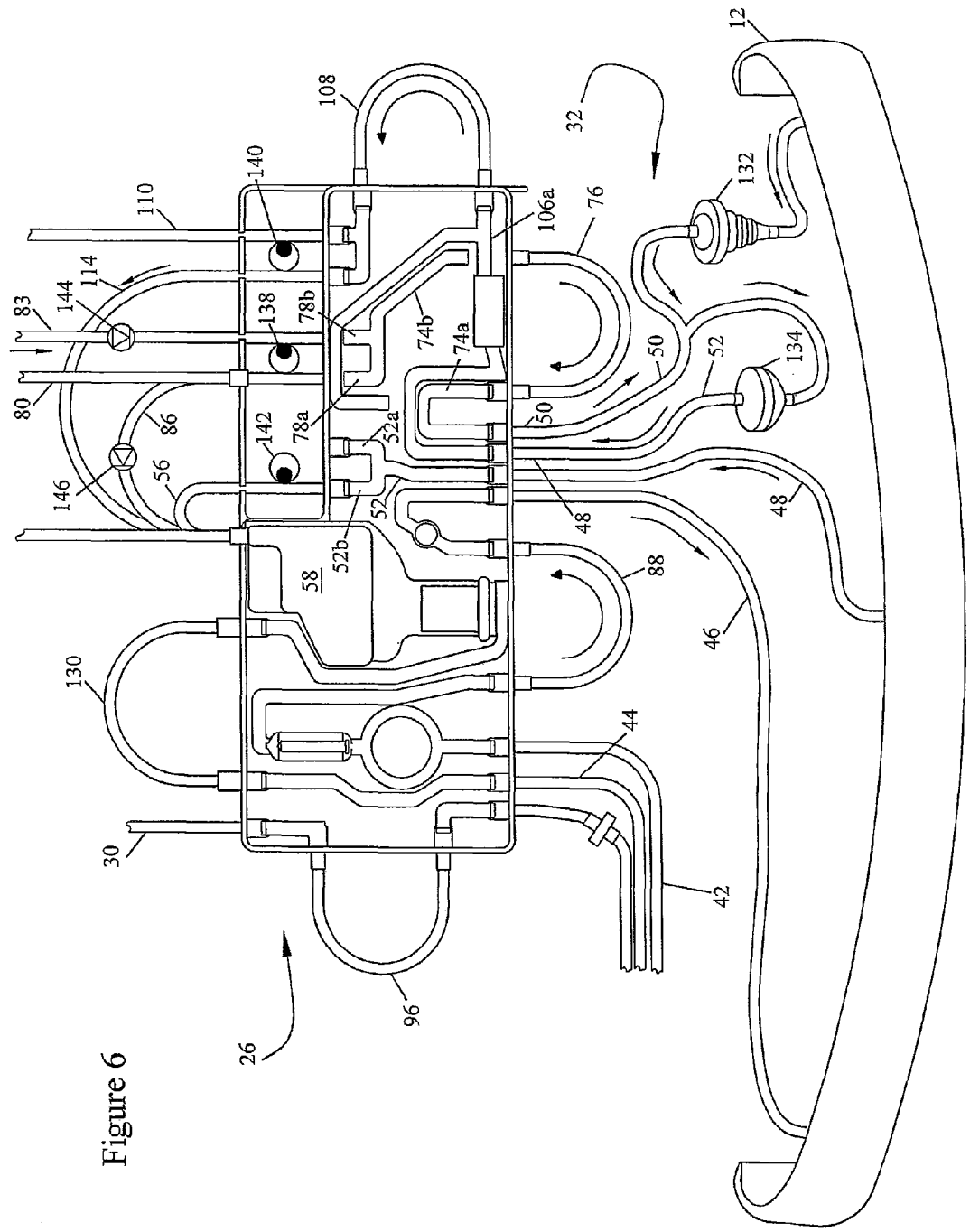
FIG. 6 shows the cassette assembly of FIG. 3 with a fourth state of fluid flow directions and valve status.

To further wash plasma out of the platelets accumulating in the concentration chamber 134, platelet additive solution (PAS) is introduced into the inflow line of the concentration chamber 134, as shown in FIG. 6. In this phase, a valve 142 on the pump/valve/sensor assembly 14 is rotated to close the red blood cell return loop 56. The plasma pump that engages tube 76 is run in reverse, thereby drawing PAS through the one-way valve 144 while fluid is prevented from flowing backward through return loop 136 by a second one-way valve 146. Valve 140 continues to block fluid flow in the platelet collect tube 110. In this state, PAS is drawn into the cassette 26, through the loop 76 and into the plasma tube 50. Balanced flows of PAS and a mixture of platelets and plasma from the separation chamber 132 mix and enter the inlet of the concentration chamber 134. In the concentration chamber 134, platelets continue to accumulate. A mixture of plasma and PAS is pumped through loop 108 and return loop 114 into the reservoir 58. Plasma, diluted by PAS, will be returned to the donor. The combination of two pumps and two sources of fluid entering the concentration chamber 134, allows control of the mixture of components in the concentration chamber. Moreover, platelets in the concentration chamber (or another blood particle or cell type) may be washed by a continuous process with any desired volume of wash solution such as PAS. In prior cell washing apparatus, a volume of wash solution has been introduced into a bag containing a blood component. The bag and its contents have then been subjected to centrifugal force, separating the contents. The less dense fluid comprising an undesired component (e.g., plasma) and wash solution is drawn off. This process would then have been repeated until the concentration of the undesired component was reduced to a desired low level. In contrast, in the present invention, wash solution may be introduced into the collection chamber 134 in a continuous manner until the desired level of the undesired component has been achieved.

Figure 7:
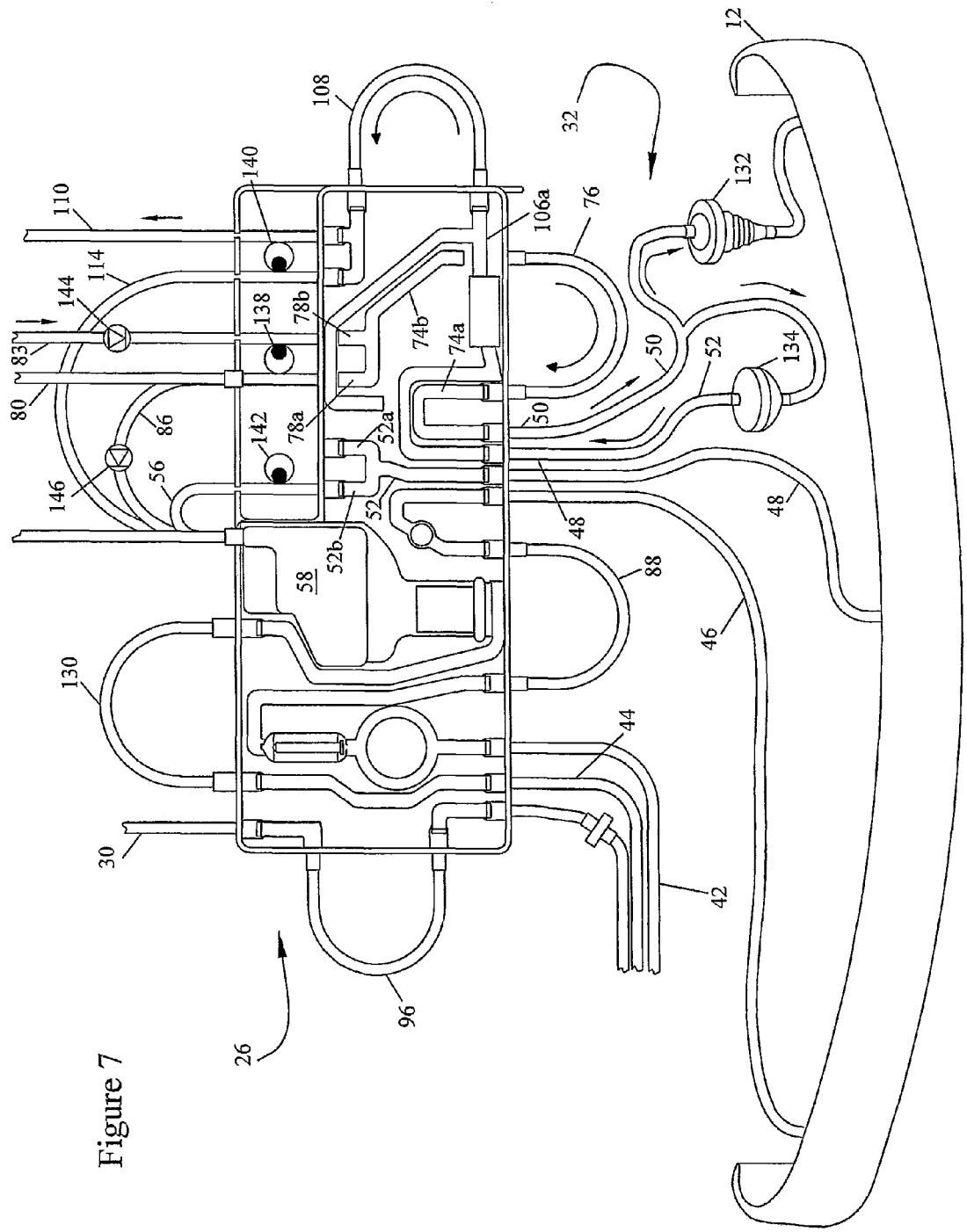
FIG. 7 shows the cassette assembly of FIG. 3 with a fifth state of fluid flow directions and valve status.

The collection of pure platelets diluted to storage concentration in PAS is shown in FIG. 7. In this phase, valve 140 opens the platelet collect line 110 and closes the return loop 114. The speed of the plasma collect pump in the reverse direction (e.g., clockwise) is increased and the whole blood pump which engages the whole blood loop 88 is stopped, thereby inhibiting further fluid flow out of the separation chamber 132 while expressing accumulated platelets out of the concentration chamber. A platelet collect pump engaging loop 108 pumps the platelets and PAS into the platelet collect tube 110 and into the platelet collect bag 40. The phases shown in FIG. 4, FIG. 5 and FIG. 6 may be repeated multiple times until a sufficient quantity of platelets has been collected.

Upon completion of collection of platelets and plasma, the collection bags 36, 40 may be separated from the rest of the set 8. The separation may be made by a clamp or by RF sealing the tubing lines 86, 110 and then separating in accordance with U.S. Pat. Nos. 5,345,070 and 5,520,218, inter alia, along the RF-sealed portion of the tubing line. Other well known methods can also be used to close the tubing lines and then separate the collection bags 36, 40 from the remainder of the disposable assembly 8.

The foregoing description of the present invention has been presented for purposes of illustration and description. Furthermore, the description is not intended to limit the invention to the form disclosed herein. Consequently, variations and modifications commensurate with the above teachings, and skill and knowledge of the relevant art, are within the scope of the present invention. The embodiments described hereinabove are further intended to explain best modes known of practicing the invention and to enable others skilled in the art to utilize the invention in such embodiment, or in such other embodiments and with various modifications required by the particular application(s) or use(s) of the present invention. It is intended that the appended claims be construed to include alternative embodiments to the extent permitted by the prior art.

What is claimed is:

1. A blood processing apparatus comprising
a centrifuge rotor having a circumferential channel housing;
a blood processing vessel adapted to fit into said channel housing, said blood processing vessel having a blood inlet and a plurality of blood component outlets;
a plasma tube coupled to one of said blood component outlets of said blood processing vessel for removing at least plasma from said blood processing vessel;
a generally frusto-conical separation chamber mounted on said centrifuge rotor and having an inlet and an outlet and being fluidly connected to said plasma tube at said inlet and connected to an outlet tube at said outlet, at least part of said outlet tube extending off of said centrifuge rotor;
a generally frusto-conical concentration chamber mounted on said centrifuge rotor, said collection chamber having an inlet and an outlet,
a concentration chamber inlet tube fluidly connected to said outlet tube of said separation chamber and to said inlet of said concentration chamber; and
a concentration chamber outlet tube fluidly connected to said outlet of said concentration chamber and extending off of said rotor.

2. The blood processing apparatus of claim 1 further comprising at least one blood component collection bag in fluid communication with said outlet tube of said concentration chamber.

3. The blood processing apparatus of claim 2 further comprising means for flushing blood components out of said concentration chamber into said at least one blood component collection bag and for simultaneously restraining fluid from flowing out of said separation chamber.

4. A disposable blood processing set for a centrifugal blood processing apparatus, said blood processing set comprising
a tubing assembly adapted to be mounted adjacent at least one of a pump, valve or sensor on a blood processing centrifuge;
a blood processing vessel fluidly connected to said tubing assembly by a plurality of tubes and adapted to be mounted on a rotor of said blood processing centrifuge, said blood processing vessel having a blood inlet and a plurality of blood component outlets;

a plasma tube coupled to one of said blood component outlets of said blood processing vessel for removing at least plasma from said blood processing vessel;

a generally frusto-conical separation chamber adapted to be mounted on said centrifuge rotor and having an inlet and an outlet and being fluidly connected to said plasma tube at said inlet and connected to an outlet tube at said outlet, said outlet tube being fluidly connected to said tube assembly;

a generally frusto-conical concentration chamber adapted to be mounted on said centrifuge rotor, said concentration chamber having an inlet and an outlet, a concentration chamber inlet tube fluidly connected to said outlet tube of said separation chamber and to said inlet of said concentration chamber; and a concentration chamber outlet tube fluidly connected to said outlet of said concentration chamber and to said tubing assembly.

5. The blood processing set of claim 4 further comprising at least one blood component collection bag in fluid communication with said outlet tube of said concentration chamber.

6. The blood processing set of claim 5 further comprising means for flushing blood components out of said concentration chamber into said at least one blood component collection bag and for simultaneously restraining fluid from flowing out of said separation chamber.

* * * * *